United States Patent [19]
Ball et al.

[11] 4,354,049
[45] Oct. 12, 1982

[54] PROCESS FOR THE PRODUCTION OF AROMATIC HYDROCARBONS

[75] Inventors: William J. Ball, Capel; David G. Stewart, Epsom, both of England

[73] Assignee: The British Petroleum Company Limited, London, England

[21] Appl. No.: 242,487

[22] Filed: Mar. 11, 1981

[30] Foreign Application Priority Data

Mar. 15, 1980 [GB] United Kingdom ................ 8008871

[51] Int. Cl.$^3$ ............................................. C10G 49/08
[52] U.S. Cl. ................................. 585/415; 208/135; 252/455 Z
[58] Field of Search .............................. 585/415, 422; 208/52 CT, 135

[56] References Cited

U.S. PATENT DOCUMENTS

| 4,056,575 | 11/1977 | Gregory et al. | 208/135 X |
| 4,112,011 | 9/1978 | Kolombos | 585/415 |
| 4,169,865 | 10/1979 | Bamforth et al. | 585/314 |
| 4,180,689 | 12/1979 | Davies et al. | 585/407 |
| 4,289,608 | 9/1981 | McArthur | 208/121 |

Primary Examiner—Delbert E. Gantz
Assistant Examiner—G. E. Schmitkons
Attorney, Agent, or Firm—Brooks, Haidt, Haffner & Delahunty

[57] ABSTRACT

A process for the production of aromatic hydrocarbons which process comprises contacting at elevated temperature and in the vapor phase a $C_2$ to $C_{12}$ aliphatic hydrocarbon feedstock with a catalyst comprising a crystalline aluminosilicate having a silica to alumina molar ratio greater than 12:1 which has been modified by incorporation therein of aluminium either by exchange or impregnation.

10 Claims, No Drawings

PROCESS FOR THE PRODUCTION OF AROMATIC HYDROCARBONS

The present invention relates to a process for the production of aromatic hydrocarbons.

The use of crystalline aluminosilicates as catalysts in hydrocarbon conversion reactions has been known for some time. Crystalline hydrated aluminosilicates, generally referred to as zeolites, may be represented by the empirical formula:

$$M_{2/n}O \cdot Al_2O_3 \cdot xSiO_2 \cdot yH_2O.$$

in which n is the valence of M which is generally an element of Group I or II, in particular sodium, potassium, magnesium, calcium, strontium or barium and x is generally equal to or greater than 2. Zeolites have skeletal structures which are made up of three-dimensional networks of $SiO_4$ and $AlO_4$ tetrahedra, cornerlinked to each other by shared oxygen atoms. There are no unshared oxygen atoms in the anionic framework so that the ratio of total aluminium and silicon atoms (Al+Si) to oxygen atoms is 1:2 and the negative charges created by the replacement of Si (IV) atoms by Al (III) atoms are neutralised by an electrochemical equivalent of cations M.

Although before the mid-1960s about 100 different types of synthetic zeolites were known it had not been found possible to synthesise zeolites having a silica to alumina molar ratio greater than about 11:1. Thereafter this was achieved by the use in the preparation of one or more quaternary alkylammonium compounds such as tetramethylammonium, tetraethylammonium, tetrapropylammonium and tetrabutylammonium compounds. There resulted a range of crystalline aluminosilicates having a silica to alumina ratio up to 2000:1, high stability, extremely high acidity and the ability to catalyse many kinds of conversion reactions, in particular the conversion of aliphatic compounds into aromatic compounds. Since that time similar types of zeolites have been synthesised from materials other than tetraalkylammonium compounds, e.g. alkanolamines.

In our British Pat. No. 1,561,590 we disclose that zeolites having a silica to alumina molar ratio of between 20:1 and 70:1 in which gallium is exchanged with the cation M or is impregnated on to the surface of the zeolite and/or into the zeolitic cavities has a surprisingly high catalytic activity in hydrocarbon conversion processes.

We have now found that crystalline aluminosilicates having a silica to alumina molar ratio greater than 12:1 and which have been modified by incorporation of aluminium either by exchange or impregnation are, surprisingly, active catalysts for the conversion of $C_2$ to $C_{12}$ aliphatic hydrocarbons to aromatic hydrocarbons.

Accordingly, the present invention provides a process for the production of aromatic hydrocarbons which process comprises contacting at elevated temperature and in the vapour phase a $C_2$ to $C_{12}$ aliphatic hydrocarbon feedstock with a catalyst comprising a crystalline aluminosilicate having a silica to alumina molar ratio greater than 12:1 which has been modified by incorporation therein of aluminium either by exchange or impregnation.

It is to be understood that the aluminium incorporated into the aluminosilicate excludes aluminium forming part of the crystal lattice of the aluminosilicate and also excludes aluminium in the form of alumina which is part or all of a matrixing material sometimes used in conjunction with crystalline aluminosilicates.

The $C_2$ to $C_{12}$ aliphatic hydrocarbon feedstock may be a single hydrocarbon or a mixture of hydrocarbons. Furthermore the, or each, hydrocarbon in the feedstock may be saturated or unsaturated. Preferably the hydrocarbon is a $C_3$ to $C_8$, even more preferably a $C_3$ to $C_6$ hydrocarbon. $C_4$ hydrocarbon fractions containing isobutane and/or isobutene and $C_3$ hydrocarbon fractions containing propane and/or propylene are particularly preferred.

With regard to the catalyst any crystalline aluminosilicate having a silica to alumina molar ratio greater than 12:1 may be used. Suitable crystalline aluminosilicates include the ZSM-type, for example ZSM-5, ZSM-11, ZSM-12, ZSM-21 and ZSM-35, which are extensively described in a number of publications including U.S. Pat. Nos.: 3,702,886, 3,709,979 and 3,970,544 and DS No. 2,213,109, all to Mobil Oil Corporation. These are generally prepared by crystallising a mixture containing a source of alumina, a source of silica, a source of alkali metal, water and a tetralkylammonium compound or its precursors. A disadvantage of the ZSM-type aluminosilicates with regard to cation exchange is that it is necessary to calcine the aluminosilicate either before or between exchanges. It is preferred therefore to employ other crystalline aluminosilicates which do not suffer from this disadvantage such as those described in our copending published European applications Nos.: 78300773.5 and 78300774.3 in which mono-, di- or triethanolamine or propanolamine or their precursors are used in place of tetralkylammonium compounds or their precursors. Another preferred crystalline aluminosilicate which may be used is that described in our copending unpublished European application No.: 80304334.8 (BP Case No 4896), i.e. the crystalline aluminosilicate produced by mixing a source of silica, a source of alumina, a source of alkali metal, water and a source of ammonium ions in the absence of an alcohol or alkylene oxide in the molar proportions (expressed in the case of the silica and alumina sources in terms of the equivalent moles of the oxide, in the case of the alkali metal source in terms of the equivalent moles of the hydroxide (MOH) and in the case of the source of ammonium ions in terms of free ammonia):

$SiO_2:Al_2O_3$ greater than 12:1, preferably from 20:1 to 50:1

$MOH:Al_2O_3$ in the range from 1:1 to 20:1, preferably from 2:1 to 10:1

$SiO_2:NH_3$ in the range from 1:1 to 200:1, preferably from 20:1 to 100:1 and $H_2O:MOH$ in the range from 30:1 to 300:1, preferably from 30:1 to 100:1 and maintaining the mixture at elevated temperature for a period such that crystallisation occurs. Other suitable crystalline aluminosilicates are described in published UK application No.: 2,018,232, the complete specification of British Pat. No.: 1,553,209 and the specification of U.S. application Ser. No. 655,065.

The crystalline aluminosilicate is modified by incorporation therein of aluminium either by exchange or impregnation. With regard to exchange any of the conventional ion-exchange techniques may be employed. Suitably the crystalline aluminosilicate may first of all be exchanged with ammonium ions and subsequently exchanged with aluminium ions. As mentioned hereinbefore, using aluminosilicates derived from quaternary alkylammonium compounds a calcination step is necessary. The exchange with ammonium ions may suitably be effected with an aqueous solution of an ammonium salt, such as the chloride. The exchange with aluminium ions may suitably be effected with an aluminium salt such as the sulphate, nitrate, acetate or a halide, e.g. the chloride. After exchange the crystalline aluminosilicate modified by incorporation of exchanged aluminium may suitably be dried.

Alternatively the crystalline aluminosilicate may be modified by incorporation of aluminium therein by impregnation. Conventional impregnation techniques may be used to produce this form of the catalyst. The impregnation may suitably be conducted by preparing a solution, suitably an aqueous solution of an aluminium salt such as for example aluminium nitrate and adding the crystalline aluminosilicate to this aqueous solution accompanied by stirring to form a paste. The paste may thereafter be dried. It is believed that the aluminium is incorporated on the surface of the aluminosilicate, in the intracrystalline cavities and, inevitably to some extent, as exchanged cations.

Whichever method of catalyst preparation is used, the amount of aluminium present may suitably be in the range from 0.1 to 10%, preferably in the range from 0.5 to 7% by weight of the crystalline aluminosilicate present.

The catalyst may suitably be activated prior to contact with the aliphatic hydrocarbon. Activation may be carried out by heating the catalyst at a temperature in the range from 400° to 650° C., preferably in the range from 500° to 600° C. Activation may be conducted in an atmosphere of hydrogen, air or a gas which is substantially inert under the reaction conditions such as nitrogen. The catalyst may suitably be used in the form of a fixed or a fluidised bed.

The elevated temperature at which the aliphatic hydrocarbon is contacted with the catalyst may suitably be in the range 450° to 700° C., preferably in the range 500° to 600° C.

The process is preferably operated continuously.

A substantially inert diluent such as nitrogen may be employed.

The invention will now be described with reference to the following Example.

In the following examples reference will be made to Ludox Type AS40 silica sol which is a silica sol containing 40% wt/wt silica and having ammonium ions as the stabilising counter ions. The silica to ammonium ratio (i.e. $SiO_2:NH_3$) is 80:1 molar.

PREPARATION OF CATALYSTS

Catalyst A (i) Alumina, Laporte Type A (13.35 g) was dissolved in a solution of sodium hydroxide (26.25 g) in deionised water (187.5 ml) by warming. This solution was then added with stirring to Ludox silica sol, Grade AS40 (590 g) and 0.910 aqueous ammonia solution (9.0 ml, containing 25% wt/wt ammonia). The pH of the mixture was 13.1.

The mixture was placed in a stirred stainless steel autoclave and heated at 170° C. for 60 hours. A crystalline aluminosilicate product was formed. The solid product was filtered and ion-exchanged by refluxing with one molar ammonium chloride solution (500 ml). This operation was repeated twice. The mixture was filtered and the solid washed with deionised water and dried at 120° C. for 16 hours.

(ii) 20 g of the dry powder were mixed with Ludox silica sol, Grade A 40 (15 g) and sufficient deionised water to form a thick paste. The whole was dried at 120° C. for 16 hours and broken down to form 5 to 16 mesh (BSS) granules. The catalyst was activated by calcining in air at 500° C. for 16 hours.

Catalyst B 15 g of the aluminosilicate prepared as described under Catalyst A(i) above were ion-exchanged by heating with a solution of aluminium nitrate nonahydrate (12.5 g) in deionised water (300 ml) with stirring for 1 hour. This operation was carried out three times. The mixture was filtered and the solid washed with deionised water (300 ml) and dried at 120° C. for 16 hours.

10 g of the dry powder were mixed with Ludox silica sol, Grade AS40 (10 g) to form a paste. The whole was dried at 120° C. for 16 hours and broken down to form 5 to 16 mesh (BSS) granules. The catalyst was activated by calcining in air at 500° C. for 16 hours.

Catalyst C (i) Sodium aluminate (12.4 g, 90% purity=0.07 mole alumina) was dissolved in a solution of sodium hydroxide (4.43 g, 0.111 mole) in deionised water (200 g, 11.11 mole). The solution was filtered and then added to diethanolamine (116.1 g, 1.106 mole) at 40° C. Ludox colloidal silica (317.3 g, containing 40% silica, 2.115 mole) disolved in deionised water (176.4 g, 9.8 mole) was then added with stirring and stirring was continued for a further 30 minutes. The mixture was transferred to a one liter autoclave and heated at 170° C. for 7 days. The pressure recorded was 10 bars. A crystalline aluminosilicate product was formed. The solid product was filtered, washed with deionised water and then ion-exchanged by refluxing with one molar ammonium chloride solution (500 ml). This operation was carried out twice. The mixture was filtered and the solid washed with deionised water and dried at 120° C. for 16 hours.

(ii) 20 g of the dry powder prepared as described above were mixed with Ludox silica sol, Grade AS40 (20 g, containing 40% wt silica) and sufficient deionised water to form a thick paste. The whole was dried at 120° C. for 16 hours and broken down to form 5 to 16 mesh (BSS) granules. The catalyst was activated by calcining in air at 500° C. for 16 hours.

Catalyst D 10 g of the aluminosilicate prepared as described under Catalyst C(i) above was ion-exchanged by refluxing with a solution of aluminum nitrate nonahydrate (10.75 g) in deionised water (60 ml) for 4 hours. The mixture was filtered and the solid washed with deionised water (250 ml) and dried at 120° C. for 16 hours.

10 g of the dry powder was mixed with Ludox silica sol, Grade AS40 (10 g) to form a paste. The whole was dried at 120° C. for 16 hours and broken down to form 5 to 16 mesh (BSS) granules. The catalyst was activated by calcining in air at 500° C. for 16 hours.

TESTING OF CATALYSTS

EXAMPLE 1

The activity of Catalyst B was tested by passing a gaseous feed of a $C_3$ hydrocarbon mixture (78.1% propane, 19.1% propylene and 2.8% ethane) over the catalyst in a heated glass reactor. The conditions used and the results obtained are given in the following Tables 1A and 1B respectively.

COMPARISON TEST 1

The Example was repeated except that Catalyst B was replaced by Catalyst A. The conditions used and the results obtained are given in the following Tables 1A and 1B respectively. This is not an example according to the invention because the crystalline aluminosilicate was not modified by incorporation of aluminium. It is included only for the purpose of comparison.

EXAMPLE 2

The activity of Catalyst D was tested by passing a gaseous feed of propane over the catalyst in a heated glass reactor. The conditions used and the results obtained are given in Tables 2A and 2B.

TABLE 1A

| | CONDITIONS USED | | | |
|---|---|---|---|---|
| Example | Catalyst | Hours on Stream | Reaction Temperature °C. | Contact[1] Time sec |
| Comp. Test 1 | A | 2 | 550 | 17.9 |

TABLE 1A-continued

| | CONDITIONS USED | | | |
|---|---|---|---|---|
| Example | Catalyst | Hours on Stream | Reaction Temperature °C. | Contact[1] Time sec |
| Example 1 | B | 2 | 550 | 16.2 |

TABLE 2A

| | CONDITIONS USED | | | |
|---|---|---|---|---|
| Example | Catalyst | Hours on Stream | Reaction Temperature °C. | Contact[1] Time sec |
| Comp. Test 2 | C | 2 | 550 | 13.0 |
| Example 2 | D | 2 | 550 | 16.0 |

With reference to the above Tables 1A and 2A:

[1]Contact time = $\dfrac{\text{Volume of catalyst in mls}}{\text{Total volume of gas (in mls/sec at NTP)}}$

TABLE 1B

| | | RESULTS OBTAINED | | | | | | | |
|---|---|---|---|---|---|---|---|---|---|---|
| | | $C_3$ conversion | Molar Yields %[3] | | | | Selectivity to | Composition of Aromatics %[5] | | |
| Example | Catalyst | %[2] | $CH_4$ | $C_2H_4$ | $C_2H_6$ | Aromatics | Aromatics[4] | Benzene | Toluene | Xylene |
| Comp. Test 1 | A | 58 | 15 | 2 | 15 | 26 | 45 | 15 | 28 | 18 |
| Example 1 | B | 89 | 22 | 3 | 12 | 52 | 58 | 33 | 35 | 11 |

With reference to the above Table

[2]$C_3$ Conversion = $\dfrac{\text{Moles of } C_3 \text{ hydrocarbon consumed}}{\text{Moles of } C_3 \text{ hydrocarbon fed}} \times 100$

[3]Molar Yield = $\dfrac{\text{Moles of } C_3 \text{ hydrocarbon converted to particular product}}{\text{Moles of } C_3 \text{ hydrocarbon fed}} \times 100$

[4]Selectivity = $\dfrac{\text{Moles of } C_3 \text{ hydrocarbon converted to aromatics}}{\text{Moles of } C_3 \text{ hydrocarbon consumed}} \times 100$

[5]Remainder poly alkyl aromatics.

TABLE 2B

| | | RESULTS OBTAINED | | | | | | | | |
|---|---|---|---|---|---|---|---|---|---|---|
| | | $C_3$ conversion | Molar Yields %[3] | | | | Selectivity to | Composition of Aromatics %[5] | | |
| Example | Catalyst | %[2] | $CH_4$ | $C_2H_4$ | $C_2H_6$ | Aromatics | Aromatics[4] | Benzene | Toluene | Xylene |
| Comp. Test 2 | C | 67 | 18 | 5 | 12 | 32 | 48 | 28 | 46 | 21 |
| Example 2 | D | 83 | 18 | 3 | 12 | 50 | 60 | 29 | 41 | 16 |

With reference to the above Table.

[2]$C_3$ Conversion = $\dfrac{\text{Moles of } C_3 \text{ hydrocarbon consumed}}{\text{Moles of } C_3 \text{ hydrocarbon fed}} \times 100$

[3]Molar Yield = $\dfrac{\text{Moles of } C_3 \text{ hydrocarbon converted to particular product}}{\text{Moles of } C_3 \text{ hydrocarbon fed}} \times 100$

[4]Selectivity = $\dfrac{\text{Moles of } C_3 \text{ hydrocarbon converted to aromatics}}{\text{Moles of } C_3 \text{ hydrocarbon consumed}} \times 100$

[5]Remainder poly alkyl aromatics.

COMPARISON TEST 2

The Example was repeated except that Catalyst D was replaced by Catalyst C. The conditions used and the results obtained are given in Tables 2A and 2B respectively. This is not an example according to the invention because the crystalline aluminosilicate was not modified by incorporation of aluminium. It is included only for the purpose of comparison The results using Catalyst B illustrate that incorporating aluminium into the zeolite prepared by the method described in our copending unpublished European Application No.: 80304334.8 produces a catalyst which is much more active for the dehydrocyclodimerisation of $C_3$ hydrocarbons into aromatics than the untreated zeolite.

The results using catalyst D demonstrate that incorporating aluminium into the zeolite prepared by the method described in our copending published European Application No: 78300774.3 produces a catalyst which is more active for the dehydrocyclodimerisation of $C_3$ hydrocarbons into aromatics than the untreated zeolite.

We claim:

1. A process for the production of aromatic hydrocarbons which process comprises contacting at elevated temperature and in the vapour phase a $C_2$ to $C_{12}$ aliphatic hydrocarbon feedstock with a catalyst comprising a crystalline aluminosilicate having a silica to alumina molar ratio greater than 12:1 which has been modified by incorporation therein of aluminium either by exchange or impregnation.

2. A process according to claim 1 wherein the feedstock is a $C_3$ to $C_6$ hydrocarbon.

3. A process according to either claim 1 or claim 2 wherein the feedstock is a $C_4$ hydrocarbon fraction containing isobutane and/or isobutene.

4. A process according to either claim 1 or claim 2 wherein the feedstock is a $C_3$ hydrocarbon fraction containing propane and/or propylene.

5. A process according to claim 1 or claim 2 wherein the crystalline aluminosilicate having a silica to alumina molar ratio greater than 12:1 is the crystalline aluminosilicate produced by crystallising a mixture containing a source of alumina, a source of silica, a source of alkali metal, water and a tetraalkylammonium compound or its precursors.

6. A process according to claim 1 or claim 2 wherein the crystalline aluminosilicate having a silica to alumina molar ratio greater than 12:1 is the crystalline aluminosilicate produced by crystallising a mixture containing a source of alumina, a source of silica, a source of alkali metal, water and a mono-, di- or tri-ethanolamine or propanolamine or their precursors.

7. A process according to claim 1 or claim 2 wherein the crystalline aluminosilicate having a silica to alumina molar ratio greater than 12:1 is the crystalline aluminosilicate produced by mixing a source of silica, a source of alumina, a source of alkali metal, water and a source of ammonium ions in the absence of an alcohol or alkylene oxide in the molar proportions (expressed in the case of silica and alumina sources in terms of the equivalent moles of the oxide, in the case of the alkali metal source in terms of the equivalent moles of the hydroxide (MOH) and in the case of the source of ammonium ions in terms of free ammonia):

$SiO_2:Al_2O_3$ greater than 12:1
$MOH:Al_2O_3$ in the range from 1:1 to 20:1
$SiO_2:NH_3$ in the range from 1:1 to 200:1, and
$H_2O:MOH$ in the range from 30:1 to 300:1 and maintaining the mixture at elevated temperature for a period such that crystallisation occurs.

8. A process according to claim 1 or claim 2 wherein the amount of aluminium incorporated is in the range from 0.1 to 10% by weight of the crystalline aluminosilicate.

9. A process according to claim 1 or claim 2 wherein the aliphatic hydrocarbon is contacted with the catalyst at a temperature in the range 450° to 700° C.

10. A process according to claim 1 or claim 2 when operated continuously.

* * * * *